United States Patent
Hanning

(10) Patent No.: US 10,740,552 B2
(45) Date of Patent: Aug. 11, 2020

(54) INTRA-SURGICAL DOCUMENTATION SYSTEM

(71) Applicant: Stryker Corporation, Kalamazoo, MI (US)

(72) Inventor: Steven Michael Hanning, Ben Lomond, CA (US)

(73) Assignee: Stryker Corporation, Kalamazoo, MI (US)

( * ) Notice: Subject to any disclaimer, the term of this patent is extended or adjusted under 35 U.S.C. 154(b) by 2 days.

(21) Appl. No.: 14/853,289

(22) Filed: Sep. 14, 2015

(65) Prior Publication Data

US 2016/0103810 A1  Apr. 14, 2016

Related U.S. Application Data

(60) Provisional application No. 62/061,398, filed on Oct. 8, 2014.

(51) Int. Cl.
*G06F 40/186* (2020.01)
*G06F 3/16* (2006.01)
(Continued)

(52) U.S. Cl.
CPC ............ *G06F 40/186* (2020.01); *A61B 34/25* (2016.02); *G06F 3/167* (2013.01); *G06F 40/169* (2020.01);
(Continued)

(58) Field of Classification Search
CPC .............................. G06F 17/24; G06F 17/243
(Continued)

(56) References Cited

U.S. PATENT DOCUMENTS 3,744,479 A   7/1973 Stein et al.
6,031,526 A   2/2000 Shipp
(Continued)

FOREIGN PATENT DOCUMENTS

JP   2002-282213 A   10/2002
JP   2002-311985 A   10/2002
WO   WO 00/08585 A2   2/2000

OTHER PUBLICATIONS

"Template;" American Heritage Dictionary; 2004; Houghton Mifflin Company; Fourth Edition; p. 1419.*
(Continued)

*Primary Examiner* — Andrew R Dyer
(74) *Attorney, Agent, or Firm* — Morrison & Foerster LLP

(57) ABSTRACT

A method of creating a surgical operative note during a specific surgical procedure on a patient. The method includes creating surgical checklists for a plurality of surgical procedures before initiation of the surgical procedure, creating an index of image specific annotations for the specific surgical procedure before initiation of the surgical procedure, obtaining an electronic template, inserting one of the surgical checklists into the template associated with the specific surgical procedure on the patient, obtaining an image of the patient, inserting the image of the patient into the electronic template, using a voice command to associate at least one of the image specific annotations with the image of the patient in the electronic template, and inserting the at least one of the image specific annotations into the electronic template adjacent the image.

16 Claims, 7 Drawing Sheets

(51) Int. Cl.
  *G16H 20/40*   (2018.01)
  *G16H 30/20*   (2018.01)
  *A61B 34/00*   (2016.01)
  *G16H 40/20*   (2018.01)
  *G16H 15/00*   (2018.01)
  *G06F 40/169*  (2020.01)

(52) U.S. Cl.
  CPC ............. *G16H 15/00* (2018.01); *G16H 20/40* (2018.01); *G16H 30/20* (2018.01); *G16H 40/20* (2018.01); *A61B 2034/256* (2016.02)

(58) Field of Classification Search
  USPC ........................................ 715/221, 224, 226
  See application file for complete search history.

(56) References Cited

U.S. PATENT DOCUMENTS

| | | | | |
|---|---|---|---|---|
| 6,090,045 | A * | 7/2000 | Leahy | A61B 5/00 |
| | | | | 128/898 |
| 6,463,426 | B1 * | 10/2002 | Lipson | G06K 9/6206 |
| 6,514,201 | B1 | 2/2003 | Greenberg | |
| 6,743,175 | B2 | 6/2004 | Greenberg | |
| 6,766,297 | B1 | 7/2004 | Lamer et al. | |
| 6,951,541 | B2 | 10/2005 | Desmarais | |
| 7,716,072 | B1 * | 5/2010 | Green, Jr. | G06F 19/328 |
| | | | | 705/3 |
| 8,015,145 | B2 * | 9/2011 | Liu | G06N 5/02 |
| | | | | 706/53 |
| 8,050,938 | B1 * | 11/2011 | Green, Jr. | G06Q 50/22 |
| | | | | 705/2 |
| 8,175,590 | B2 | 5/2012 | Hamel et al. | |
| 8,301,461 | B2 * | 10/2012 | Reiner | G06F 19/321 |
| | | | | 705/2 |
| 8,313,432 | B2 * | 11/2012 | Chiu | A61B 5/7289 |
| | | | | 600/300 |
| 8,443,279 | B1 | 5/2013 | Hameed et al. | |
| 8,510,126 | B2 * | 8/2013 | Martin | G06Q 50/24 |
| | | | | 705/2 |
| 8,688,459 | B2 * | 4/2014 | Nenov | A61B 5/0002 |
| | | | | 704/275 |
| 8,786,601 | B2 * | 7/2014 | Lehmann | G06T 19/00 |
| | | | | 345/427 |
| 8,918,740 | B2 * | 12/2014 | Nishiyama | A61B 1/00009 |
| | | | | 382/128 |
| 9,717,552 | B2 * | 8/2017 | Cosman | A61B 18/1482 |
| 2003/0146942 | A1 | 8/2003 | Helgason et al. | |
| 2004/0169673 | A1 * | 9/2004 | Crampe | A61B 17/1757 |
| | | | | 715/700 |
| 2005/0114140 | A1 * | 5/2005 | Brackett | G10L 15/01 |
| | | | | 704/270 |
| 2005/0125256 | A1 | 6/2005 | Schoenberg et al. | |
| 2005/0197567 | A1 * | 9/2005 | Qian | G06T 7/0012 |
| | | | | 600/425 |
| 2005/0288571 | A1 * | 12/2005 | Perkins | A61B 5/0002 |
| | | | | 600/407 |
| 2006/0143041 | A1 * | 6/2006 | Tipimeni | G06Q 10/10 |
| | | | | 705/2 |
| 2006/0184160 | A1 | 8/2006 | Ozaki et al. | |
| 2006/0200354 | A1 | 9/2006 | Ito et al. | |
| 2007/0242069 | A1 * | 10/2007 | Matsue | G06F 19/32 |
| | | | | 345/428 |
| 2007/0274585 | A1 * | 11/2007 | Zhang | G06F 19/321 |
| | | | | 382/132 |
| 2008/0154598 | A1 | 6/2008 | Smith | |
| 2008/0270341 | A1 * | 10/2008 | Youngblood | A61B 34/25 |
| 2009/0009815 | A1 * | 1/2009 | Karasik | H04N 1/00326 |
| | | | | 358/403 |
| 2009/0054755 | A1 * | 2/2009 | Shiibashi | G06F 19/321 |
| | | | | 600/407 |
| 2009/0054768 | A1 * | 2/2009 | Halmann | A61B 8/00 |
| | | | | 600/437 |
| 2009/0070140 | A1 | 3/2009 | Morsch et al. | |
| 2009/0106051 | A1 * | 4/2009 | Albro | G06Q 10/06 |
| | | | | 705/3 |
| 2009/0130641 | A1 * | 5/2009 | Mahesh | G09B 23/28 |
| | | | | 434/262 |
| 2009/0198514 | A1 * | 8/2009 | Rhodes | G06F 19/322 |
| | | | | 705/3 |
| 2009/0208076 | A1 * | 8/2009 | Nakajima | G06F 19/321 |
| | | | | 382/128 |
| 2009/0217194 | A1 * | 8/2009 | Martin | G06F 19/00 |
| | | | | 715/783 |
| 2010/0179852 | A1 * | 7/2010 | Tomizuka | G06Q 10/00 |
| | | | | 705/3 |
| 2011/0015938 | A1 * | 1/2011 | Rabinowitz | G06Q 10/00 |
| | | | | 705/2 |
| 2011/0071845 | A1 * | 3/2011 | Wagner | G06Q 50/22 |
| | | | | 705/2 |
| 2012/0130223 | A1 * | 5/2012 | Reicher | G06F 19/321 |
| | | | | 600/407 |
| 2012/0209833 | A1 * | 8/2012 | Kramer | G06F 16/583 |
| | | | | 707/723 |
| 2013/0113929 | A1 * | 5/2013 | DeLand | G06K 9/00677 |
| | | | | 348/143 |
| 2013/0179183 | A1 * | 7/2013 | Wagner | G06Q 50/22 |
| | | | | 705/2 |
| 2013/0208955 | A1 * | 8/2013 | Zhao | G06F 19/321 |
| | | | | 382/128 |
| 2013/0238358 | A1 * | 9/2013 | Yamane | G06F 19/324 |
| | | | | 705/3 |
| 2014/0006943 | A1 * | 1/2014 | Robbins | G06F 19/327 |
| | | | | 715/273 |
| 2014/0081659 | A1 * | 3/2014 | Nawana | G06F 19/00 |
| | | | | 705/3 |
| 2014/0098931 | A1 * | 4/2014 | Profio | A61B 6/03 |
| | | | | 378/19 |
| 2014/0108983 | A1 * | 4/2014 | William | A61B 5/7435 |
| | | | | 715/771 |
| 2014/0172457 | A1 * | 6/2014 | Ueda | G06F 19/321 |
| | | | | 705/3 |
| 2014/0188503 | A1 * | 7/2014 | Balignasay | G16H 10/60 |
| | | | | 705/2 |
| 2014/0378828 | A1 * | 12/2014 | Penenberg | A61B 34/25 |
| | | | | 600/424 |
| 2015/0033128 | A1 * | 1/2015 | Curd | G06F 3/167 |
| | | | | 715/728 |
| 2015/0223767 | A1 * | 8/2015 | Sehnert | A61B 6/06 |
| | | | | 378/42 |
| 2015/0262014 | A1 * | 9/2015 | Iwamura | G06F 19/321 |
| | | | | 382/128 |

OTHER PUBLICATIONS

Sidne™ Operating and Maintenance Manual, by Stryker®, published more than one year prior to the filing date of the priority application (123 pages).

Sidne™ Operating and Maintenance Manual, by Stryker® Endoscopy, published more than one year prior to the filing date of the priority application (33 pages).

Hermes™ Operating Room Control Center—Operating & Maintenance Manual, by Stryker® Endoscopy, published more than one year prior to the filing date of the priority application (46 pages).

"Hermes Voice Activated O.R. Control Center—Integrating Technology" by Stryker® Endoscopy; published in 2001 (6 pages).

* cited by examiner

INTRA-SURGICAL DOCUMENTATION SYSTEM

CROSS REFERENCE TO RELATED APPLICATION

This claims the benefit of U.S. Provisional Application Ser. No. 62/061,398, filed Oct. 8, 2014.

FIELD OF THE INVENTION

The present invention relates to a surgical process, and in particular to a method of creating a surgical operative note during a specific surgical procedure on a patient.

BACKGROUND OF THE INVENTION

Typically, after completion of a medical procedure, the physician dictates notes about the procedure, describing exactly what was done during the procedure, observations the physician made during the procedure, medications administered, etc. Such operative notes are reports written (either on a paper document or in an electronic document) to document the details of a surgery. The physician typically dictates these notes into some form of audio recording device or system. If the medical procedure was recorded on video, the physician might dictate his notes while viewing the recorded video, perhaps mentioning in his dictation the timestamps of certain key frames and what was happening in those frames. The dictation (audio recording) may be provided to a transcription service, which produces a written record of the dictation for the patient's file. The time spent creating the written record, reviewing the written record and storing the written record can be very time consuming. Therefore, a method of creating a written record of surgery in a quicker and easier manner is desired.

U.S. Pat. No. 6,031,526 to Shipp discloses a voice controlled medical text and image reporting system. Using this system, a physician issues a verbal or manual command in order to capture a selected still image from a video camera being used during a medical procedure, and dictates his or her observations concerning the medical procedure and the captured image. A voice recognition module converts the dictated audio observations into viewable and editable text which is integrated with the captured still image in a word processing module, so as to form an electronic medical record which can be edited and viewed as well as printed. However, all information and text in the electronic medical record formed using the system of Shipp must be created during or after the surgical procedure, which is inefficient from a time standpoint.

A system allowing for creation of an operative note during a surgical procedure that minimizes the effort and time to create the operative note is desired.

SUMMARY OF THE INVENTION

The present invention, according to one aspect, is directed to a method of creating a surgical operative note during a specific surgical procedure on a patient. The method involves creating surgical checklists for a plurality of surgical procedures before initiation of the surgical procedure, creating an index of image specific annotations for the specific surgical procedure before initiation of the surgical procedure, obtaining an electronic template, inserting one of the surgical checklists into the template associated with the specific surgical procedure on the patient, obtaining an image of the patient, inserting the image of the patient into the electronic template, using a voice command to associate at least one of the image specific annotations with the image of the patient in the electronic template, and inserting the at least one of the image specific annotations into the electronic template adjacent the image.

Another aspect of the present invention is directed to providing a method of creating a surgical operative note during a specific surgical procedure on a patient, including creating surgical information before initiation of the surgical procedure, creating an index of image specific annotations for the specific surgical procedure before initiation of the surgical procedure, obtaining an electronic template, inserting the surgical information into the template, obtaining an image of the patient, inserting the image of the patient into the electronic template, using a voice command to associate at least one of the image specific annotations with the image of the patient in the electronic template, inserting the at least one of the image specific annotations into the electronic template adjacent the image, dictating information related to the specific surgical procedure during the specific surgical procedure, transferring the dictated information into free text, and directly inserting the free text into the electronic template at a location in the electronic template spaced from the at least one of the image specific annotations. The free text is directly inserted into the electronic template during the specific surgical procedure.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

Figure 1A:
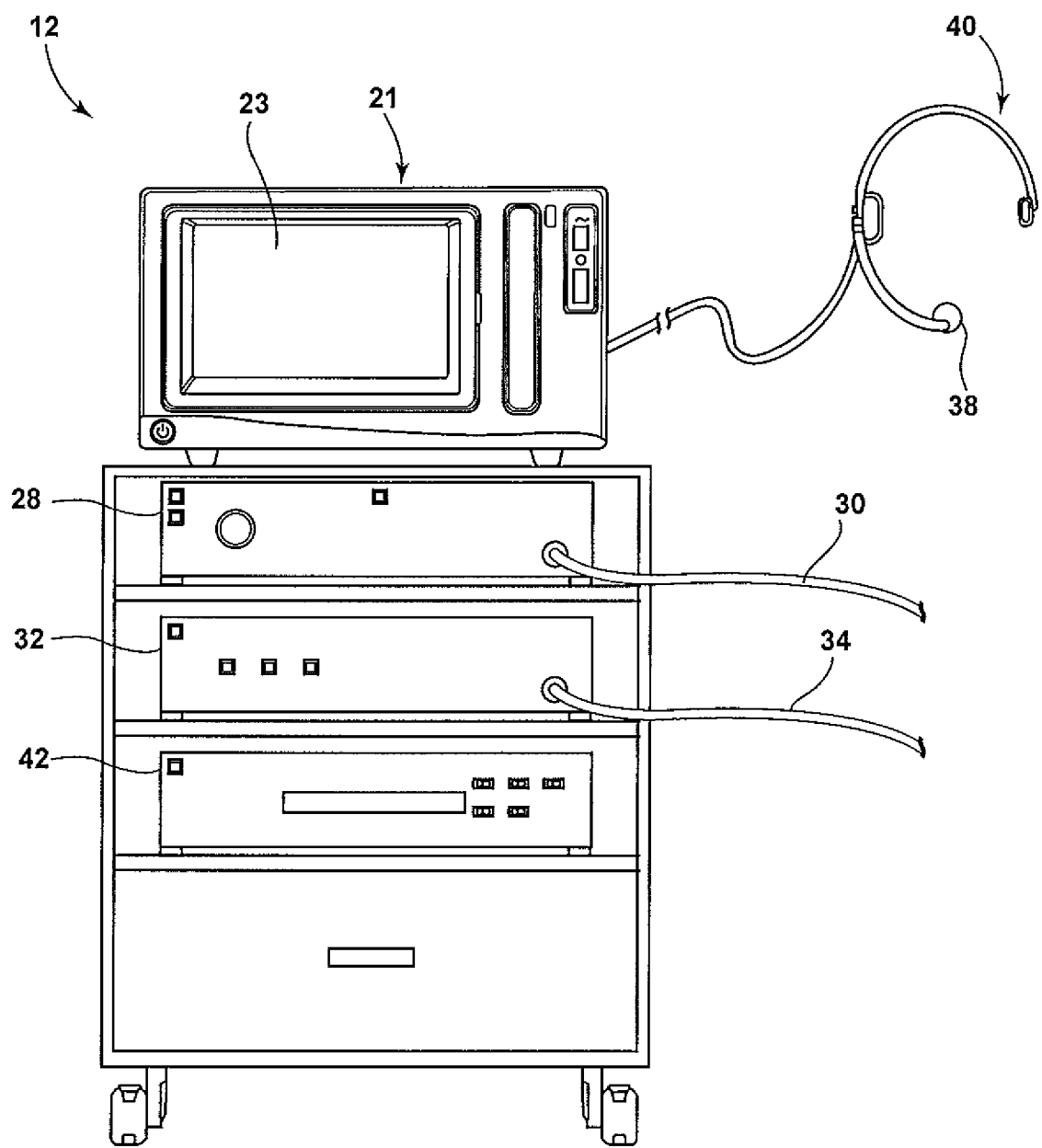
FIGS. 1A and 1B collectively show an example of an endoscopic imaging system.
Figure 1B:
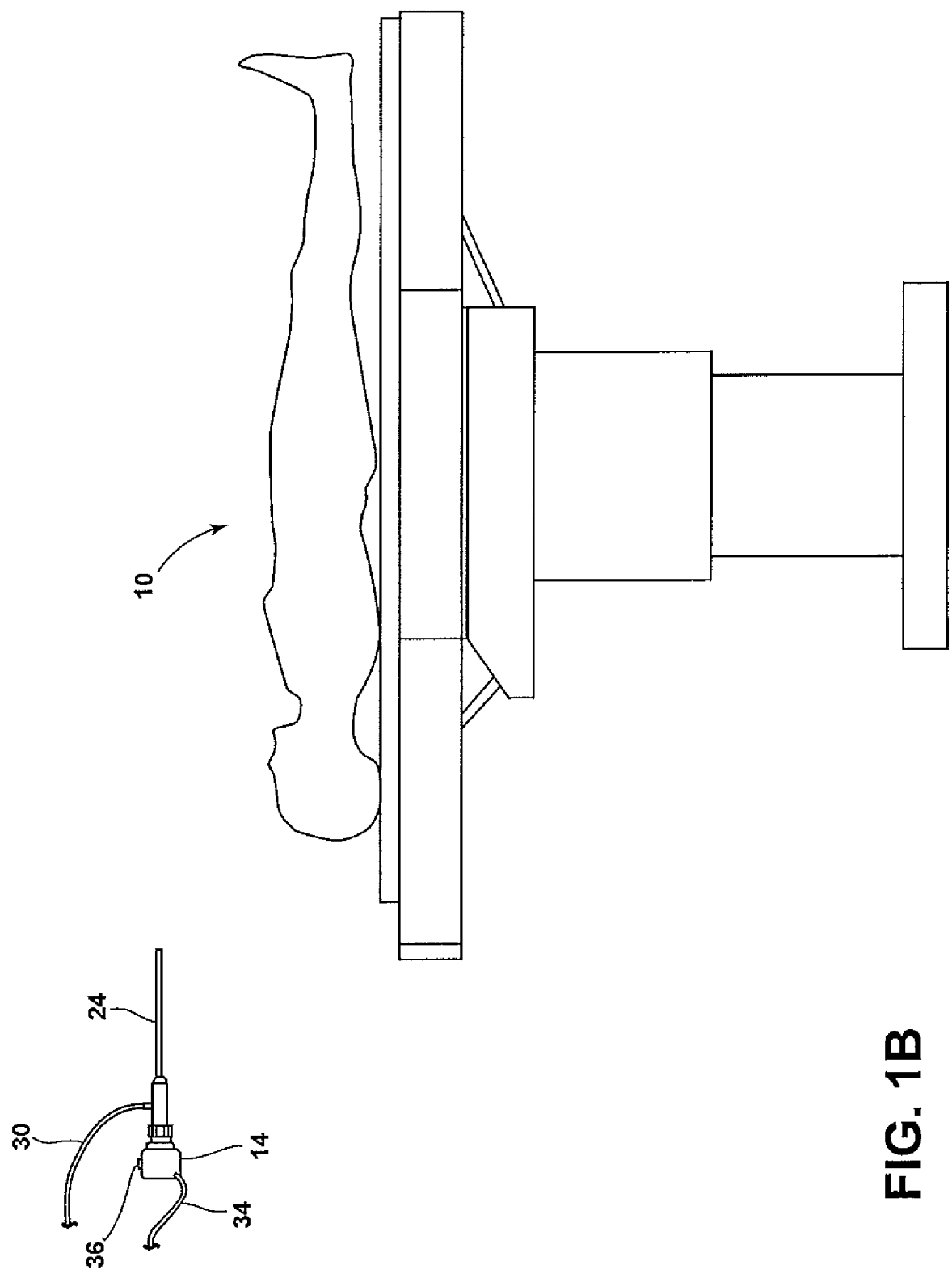
Figure 2:
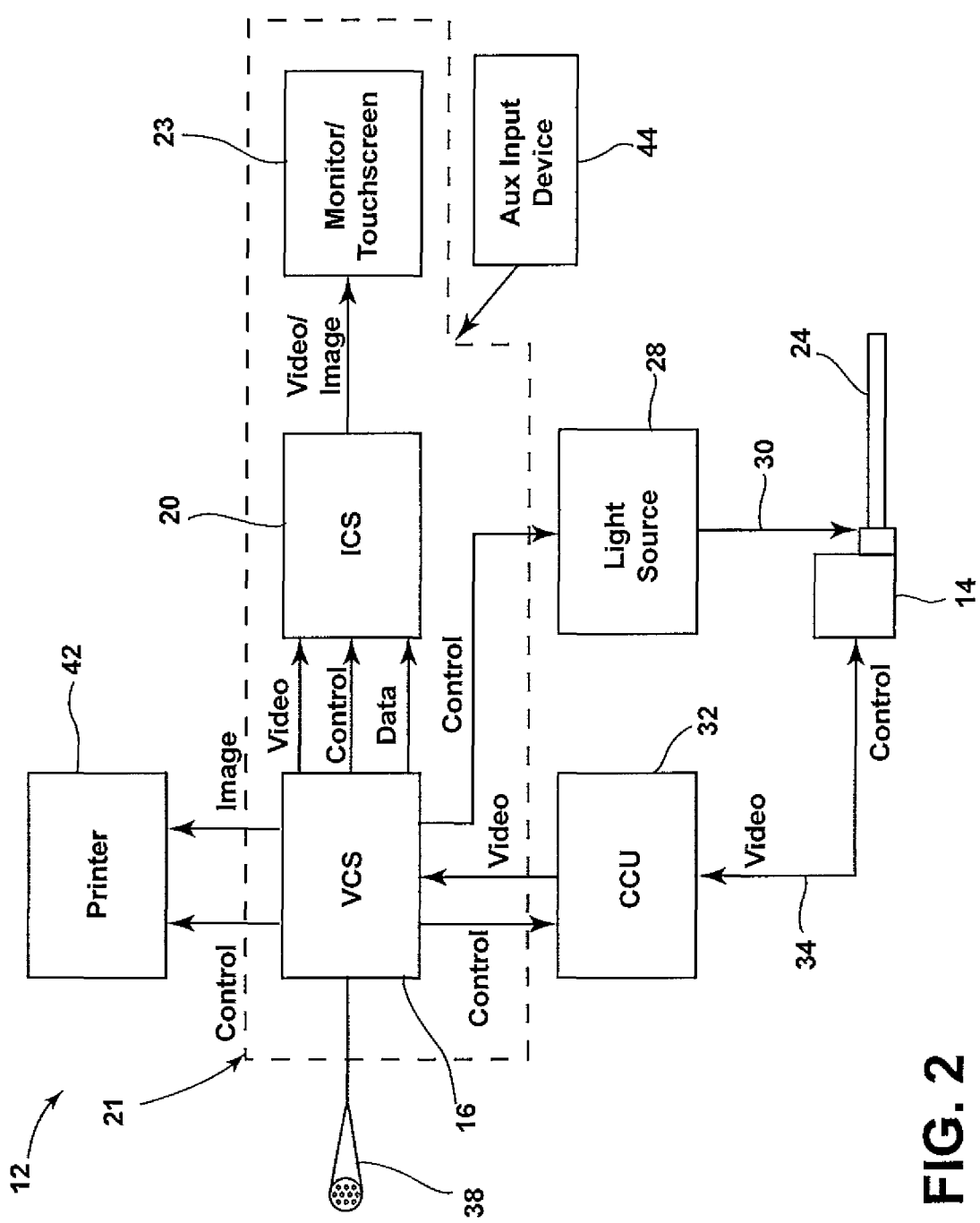
FIG. 2 is a functional block diagram of the endoscopic camera system of FIGS. 1A and 1B.

The present invention provides a method and apparatus for creating a surgical operative note 100 (see FIG. 5) during a specific surgical procedure on a patient 10 (FIG. 1B). In order to create the surgical operative note 100, an imaging system 12 is used. With reference to FIGS. 1A, 1B and 2, the imaging system 12 according to certain embodiments of the invention can include a video camera 14 and a voice control and image capture device 21. The voice control and image capture device 21 includes a voice-responsive control system (VCS) 16 and an image capture system (ICS) 20. The VCS 16 receives speech from a user (e.g., surgeon) to control functions of various components in the imaging system 12, including the ICS 20 and the video camera 14. The ICS 20 receives a video stream generated by the video camera 14 and captures video and/or still images from the video stream. In the illustrated example, the VCS 16 and the ICS 20 are integrated into the voice control and image capture device 21, which can also include a touchscreen monitor 23 (see FIGS. 1A and 2). However, the VCS 16 and the ICS 20 could be provided as separate units which communicate with each other. Other input devices 44 such as a mouse and/or a keyboard can be connected to the voice control and image capture device 21 for interaction with devices of the imaging system 12. Furthermore, the voice control and image capture device 21 can have a printer 42 connected thereto for printing images captured by the video camera 14 and a further monitor (not shown) which displays, for example, the output from the video camera 14.

FIGS. 1A, 1B and 2 collectively show an example of the imaging system 12 in which the surgical operative note 100 can be created. In the illustrated example, the imaging system 12 is an endoscopic imaging system. However, it is contemplated that the imaging system 12 could be any system that obtains or creates images of the patient 10 during a surgical procedure (e.g., from video cameras, video cassette recorders, X-ray scanners (which convert X-ray films to digital files), digital X-ray acquisition apparatus, fluoroscopes, CT scanners, MRI scanners, ultrasound scanners, ccd devices, and other types of scanners (handheld or otherwise)). The illustrated system includes an endoscope ("scope") 24 of the type commonly used for laparoscopy or arthroscopy. The scope 24 is coupled to the video camera 14, which includes well-known components for generating color video based on light received through the scope 24. High intensity light is transmitted into the patient 10 from a light source unit 28 through a fiber optic cable 30 and the scope 24. The video camera 14 is coupled to a camera control unit (CCU) 32 by a flexible electronic transmission line 34. Certain functions of the video camera 14 can be controlled from the CCU 32. The transmission line 34 conveys video data from the video camera 14 to the CCU 32 and also conveys various control signals bi-directionally between the video camera 14 and the CCU 32. One or more buttons 36 or other similar manual controls on the video camera 14 allow a user to control certain functions of the video camera 14, such as zoom and/or taking a static image for the surgical operative note 100 as described below.

Certain functions of the imaging system 12 may also be controlled by voice commands using the VCS 16. Speech from a user is can be input into the VCS 16 through a microphone 38 on a headset 40 worn by the user. The headset 40 can be wired to the voice control and image capture device 21 or can communicate wirelessly with the voice control and image capture device 21 (e.g., using Bluetooth communication or wifi communication). The VCS 16 includes an automatic speech recognition (ASR) engine 18 (see FIG. 3) to recognize and generate control signals in response to the user's speech.

Video acquired by the video camera 14 is processed by the CCU 32 and used to generate images which are displayed on the touchscreen monitor 23. The ICS 20 can record the live video and/or generate static images (i.e., captured video frames) from the live video. Hard copies of captured video frames can be printed by the printer 42 and the captured video can be used in the surgical operative note 100. The CCU 32 provides certain basic video processing functions and enables control of certain camera functions, such as control of white balance control, contrast, zoom, etc. Details of the architecture, capabilities and operation of the CCU 32 are not germane to the present invention and therefore are not described herein.

Figure 3:
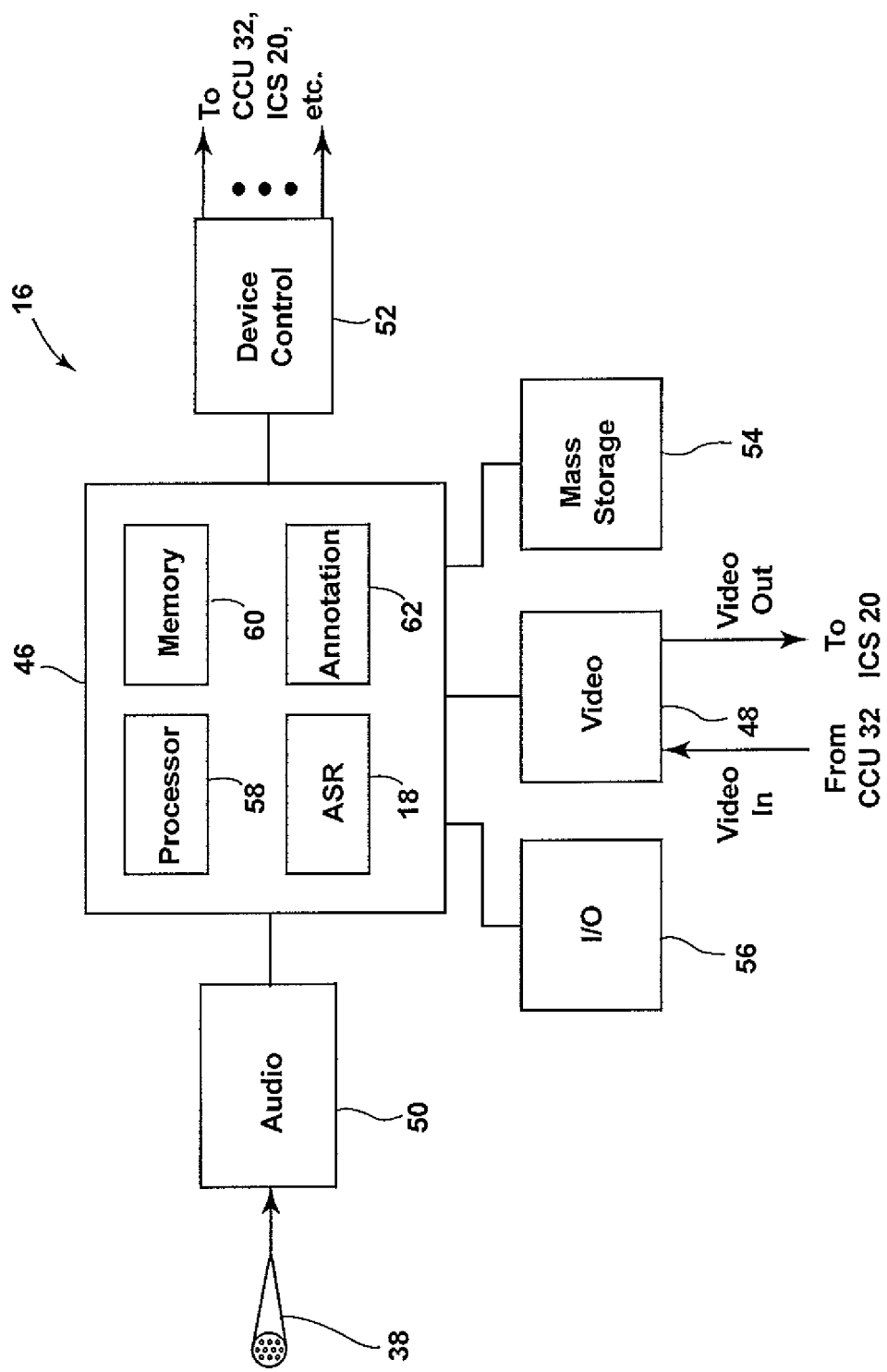
FIG. 3 is a block diagram of the voice-responsive control system (VCS).

FIG. 3 is a functional block diagram of the VCS 16 of integrated voice control and image capture device 21 of FIG. 2, according to certain embodiments of the invention. The VCS 16 provides centralized voice control of various devices and systems in the operating room, including any or all of: the CCU 32, the ICS 20, the light source unit 28, the touchscreen monitor 23, and the printer 42. For each device or system to be controlled in the operating room, the VCS 16 provides a hierarchy of commands that can be spoken by a user to control that device. By simply speaking the name of a device or system into the microphone 38, the user can access the menu of commands for that device. The VCS 16 outputs control signals to each of the voice-controllable devices. In addition, the VCS 16 provides separate video and data output signals to at least the ICS 20.

The ICS 20 of the voice control and image capture device 21 is a multi-function digital image capture device. The ICS 20 receives video generated by the video camera 14 (either directly or through one or more other devices) and provides video output to the touchscreen monitor 23 and/or an external monitor (not shown). The ICS 20 provides the ability to capture live video, i.e., to convert standard analog video into digital format (if necessary) and to record the digital video, and to capture video frames as still images. In certain embodiments, the ICS 20 also provides various other capabilities, including the ability to stream live or recorded video over a computer network. One example of an integrated voice control and image capture device 21 is the commercially available SDC3 Information Management System sold by Stryker Endoscopy of San Jose, Calif. under Model No. 0240060100.

In certain embodiments of the invention, the ability to insert images and annotate the inserted images in the surgical operative note 100 based on speech is provided by the VCS 16 in cooperation with the ICS 20. Live video generated by the video camera 14 is routed through the CCU 32 to the voice control and image capture device 21. In the voice control and image capture device 21, the live video can be routed through the VCS 16 and then to the ICS 20. Routing the video through the VCS 16 facilitates synchronization of spoken annotations with the live video stream if desired. However, it is contemplated that the live video steam can be routed simultaneously to each of the VCS 16 and the ICS 20 or directly to the ICS 20.

FIG. 3 shows the VCS 16 of the integrated voice control and image capture device 21 of FIG. 2 in greater detail. As illustrated, the VCS 16 includes a motherboard 46 coupled to a video board 48, an audio board 50, a device control interface 52, a mass storage device 54, and various I/O controls and/or indicators 56. The motherboard 46 includes one or more processors 58 or other similar control devices as well as one or more memory devices 60. The processor 58 controls the overall operation of the VCS 16 and can include hardwired circuitry, programmable circuitry that executes software, or a combination thereof. The processor 58 may, for example, execute software stored in the memory device 60. The processor 58 may include, for example, one or more general- or special-purpose programmable microprocessors and/or microcontrollers, application specific integrated circuits (ASICs), programmable logic devices (PLDs), programmable gate arrays (PGAs), or the like. The memory device 60 may include any combination of one or more random access memories (RAMS), read-only memories (ROMs) (which may be programmable), flash memory, and/or other similar storage devices.

In the illustrated embodiment, the motherboard 46 also includes an annotation module 62 to provide the VCS's 16 functionality related to annotating images, as described herein. The annotation module 62 can be hardwired circuitry, programmable circuitry that executes software, or a combination thereof. Although shown as a separate unit, the annotation module 62 can be implemented in the processor 58. The annotation module 62 can alternatively be located off the motherboard 46, such as in the device control interface 52 or the audio board 50, can be distributed between multiple boards/devices within the VCS 16, may be located on the Internet or other type of wide area network (WAN), a local area network (LAN), a corporate intranet, any other type of network, a combination of such networks, or can be stored in cloud storage retrievable through a network interface 72 of the ICS 20 of the voice control and image capture device 21 discussed below (see FIG. 4).

The illustrated video board 48 can be a conventional video input/output (I/O) interface, which includes an input to receive live video from the CCU 32 and provide the live video to the ICS 20. The audio board 50 has an input to receive speech of the user from the microphone 38. In addition, the audio board 50 includes appropriate audio processing or speech recognition circuitry such as is well-known in the art. As noted above, the VCS 16 includes an ASR engine 18, which may be implemented on the motherboard 46 (as shown), or on the audio board 50, or both. Although shown as a separate unit, the ASR engine 18 could be incorporated into the processor 58 executing appropriate software.

The device control interface 52 provides a communication interface between the VCS 16 and other voice-controllable devices or systems to allow the VCS 16 to control those devices. The device control interface 52 may include various different types of control/communication interfaces, such as a serial interface (e.g., RS-232, FireWire, or USB), Bluetooth, infrared (IR), etc. The mass storage device 54 may be any type of nonvolatile storage device capable of storing a relatively large volume of data and/or instructions, such as a magnetic or optical disk drive. The details of how devices or systems are controlled by the VCS 16 and the protocols used are not germane to the present invention and thus are not described herein.

Figure 4:
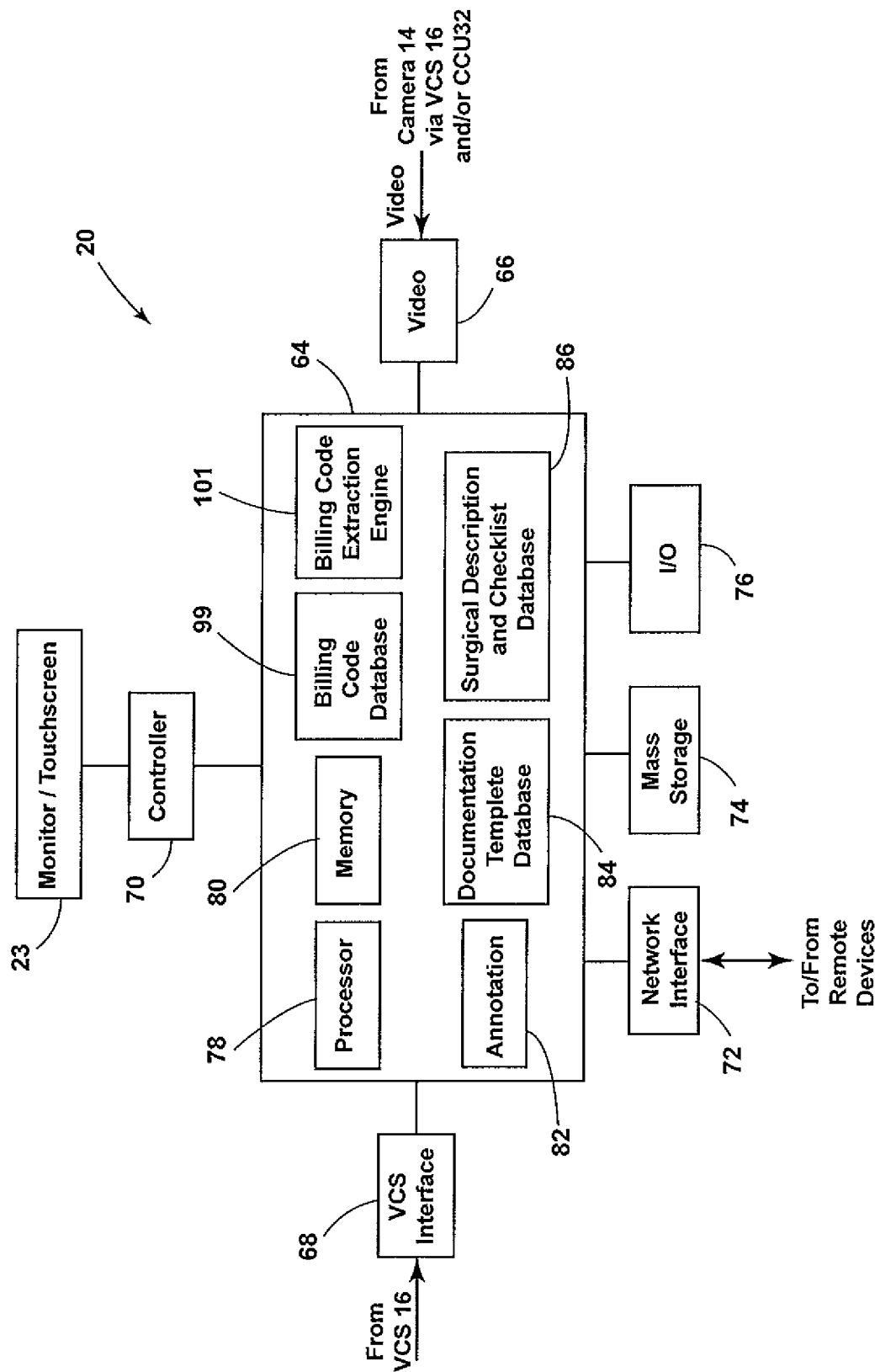
FIG. 4 is a block diagram of the image capture device (ICS).

FIG. 4 is a block diagram showing the ICS 20 of the voice control and image capture device 21 of FIG. 2 in greater detail. As illustrated, the ICS 20 includes a motherboard 64 coupled to a video board 66, a VCS interface 68, the touchscreen monitor 23 (coupled to the motherboard 64 via a display controller 70), a network interface 72, a mass storage device 74, and various I/O controls and/or indicators 76. The motherboard 64 includes one or more processors 78 or other similar control devices as well as one or more memory devices 80. The processor 78 controls the overall operation of the ICS 20 and can include hardwired circuitry, programmable circuitry that executes software, or a combination thereof. The processor 78 may, for example, execute software stored in the memory device 80. The processor 78 may be, for example, one or more general- or special-purpose programmable microprocessors and/or microcontrollers, ASICs, PLDs, PGAs, or the like. The memory device 80 may include any combination of one or more random access memories (RAMs), read-only memories (ROMs) (which may be programmable), flash memory, and/or other similar storage devices.

In the illustrated embodiment, the motherboard 64 also includes an annotation module 82 to provide the functionality of the ICS 20 related to annotating video, as described herein. The annotation module 82 can be hardwired circuitry, programmable circuitry that executes software, or a combination thereof. Although shown as a separate unit, the annotation module 82 can be implemented in the processor 78. The annotation module 82 can alternatively be located off the motherboard 64, such as in the VCS interface 68 or the video board 66, can be distributed between multiple boards/devices within the ICS 20, may be located on the Internet or other type of wide area network (WAN), a local area network (LAN), a corporate intranet, any other type of network, a combination of such networks, or can be stored in cloud storage retrievable through the network interface 72 of the ICS 20.

The illustrated motherboard 64 also includes a documentation template database 84 and a surgical description and checklist database 86 to provide the functionality of the ICS 20 related to creating the surgical operative note 100, as described herein. The documentation template database 84 and the surgical description and checklist database 86 can be hardwired circuitry, programmable circuitry that executes software, or a combination thereof. Although shown as separate units, the documentation template database 84 and the surgical description and checklist database 86 can each be implemented in the processor 78. The documentation template database 84 and the surgical description and checklist database 86 can alternatively be located off the motherboard 64, such as in the VCS interface 68 or the video board 66, can be distributed between multiple boards/devices within the ICS 20, may be located on the Internet or other type of wide area network (WAN), a local area network (LAN), a corporate intranet, any other type of network, a combination of such networks, or can be stored in cloud storage retrievable through the network interface 72.

In the illustrated example, the motherboard 64 can further include a surgical billing code database 99. The surgical billing code database 99 can include a list of billing codes that can help a hospital or similar entity bill a patient (directly or indirectly (e.g., through an insurance provider)) for the services performed on the patient. The billing codes can be standardized codes (e.g., from the International Classification of Diseases (ICD) (e.g., ICD 9 or ICD 10) or Current Procedural Terminology (CPT)) or can be codes created by the hospital or similar entity. As outlined below, the surgical billing code database 99 can supply billing codes to a billing code extraction engine 101 tied to the annotation modules 62 and/or 82 to automatically populate the surgical operative note 100 with billing codes when an annotation or particular text is added to the surgical operative note 100. The surgical billing code database 99 can alternatively be located off the motherboard 64, such as in the VCS interface 68 or the video board 66, can be distributed between multiple boards/devices within the ICS 20, may be located on the Internet or other type of wide area network (WAN), a local area network (LAN), a corporate intranet, any other type of network, a combination of such networks, or can be stored in cloud storage retrievable through the network interface 72.

The touchscreen monitor 23 is used to provide a user-friendly, touch-sensitive, graphical user interface. The VCS interface 68 is used to receive control signals and data from the VCS 16. The display controller 70 provides output to the touchscreen monitor 23 and/or to the external monitor, for display. The network interface 72 allows video, still images, electronic messages, and other information to be communicated to or from remote devices over a network.

The video board 66 receives the live video stream from the video camera 14 (via the VCS 16 and/or the CCU 32) and includes video capture circuitry to convert input analog video into digital format (if the input video is not already in digital format) and to capture still images of individual video frames. The mass storage device 74 can be used to store recorded video, captured still images, predefined annotations in an index as outlined below, related metadata, and the surgical operative note 100. The predefined annotations in the index can also be stored in a database on the Internet or other type of wide area network (WAN), a local area network (LAN), a corporate intranet, any other type of network, a combination of such networks, or can be stored in cloud storage retrievable through the network interface 72 of the ICS 20.

Figure 5:
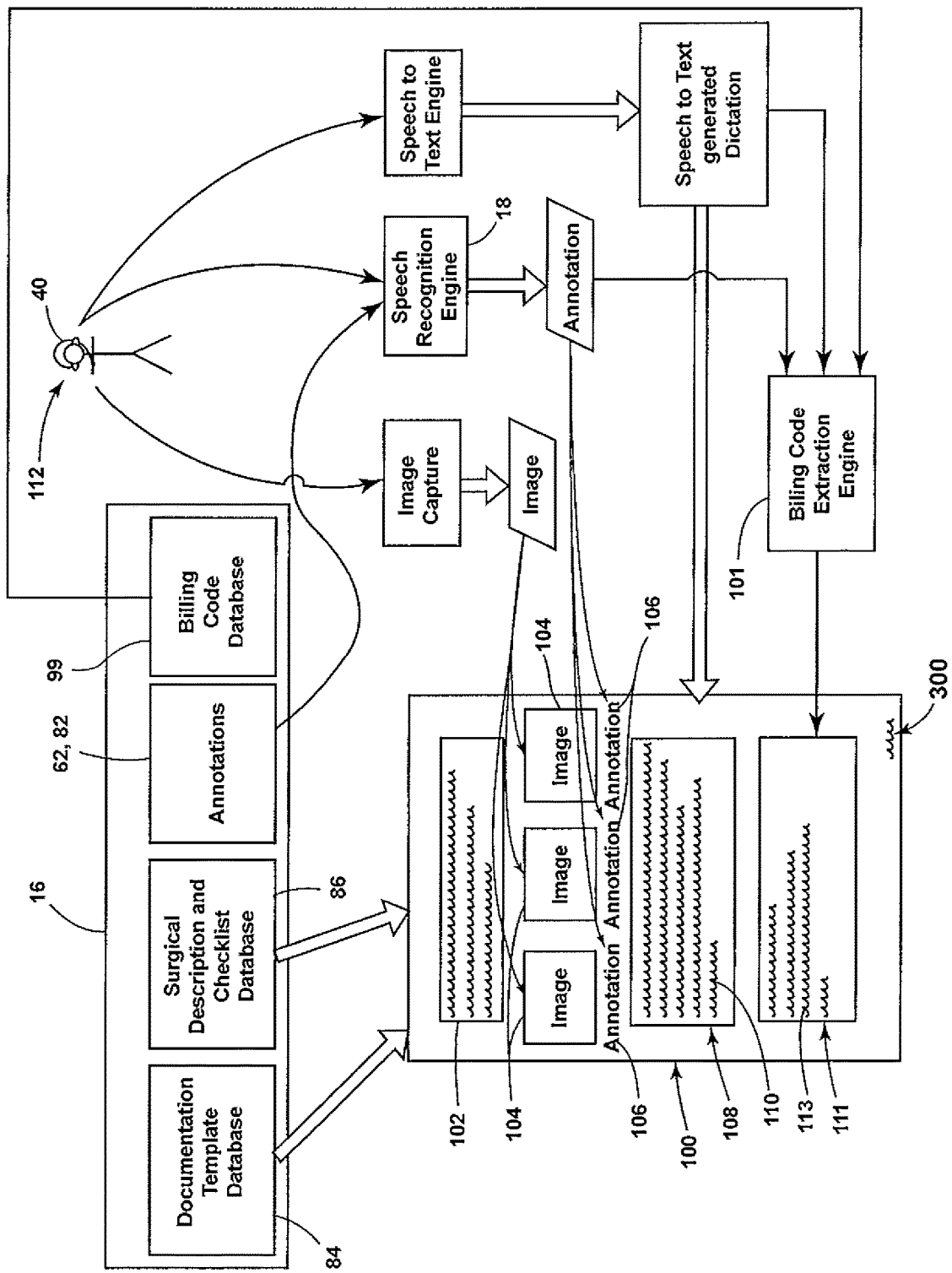
FIG. 5 is a schematic process for creating a surgical operative note of the present invention.

FIG. 5 illustrates a schematic process for creating the surgical operative note 100 of the present invention. The surgical operative note 100 includes a surgical description and checklist 102 for a particular surgical procedure, a plurality of images 104 taken from the video camera 14, an annotation 106 for each image 104, a free text area 108 having dictated text 110 therein and a further text area 111 having predetermined text 113 entered therein. The surgical operative note 100 is created during a specific surgical procedure on the patient 10 such that the surgical operative note 100 can be complete before the end of the specific surgical procedure.

Figure 6:
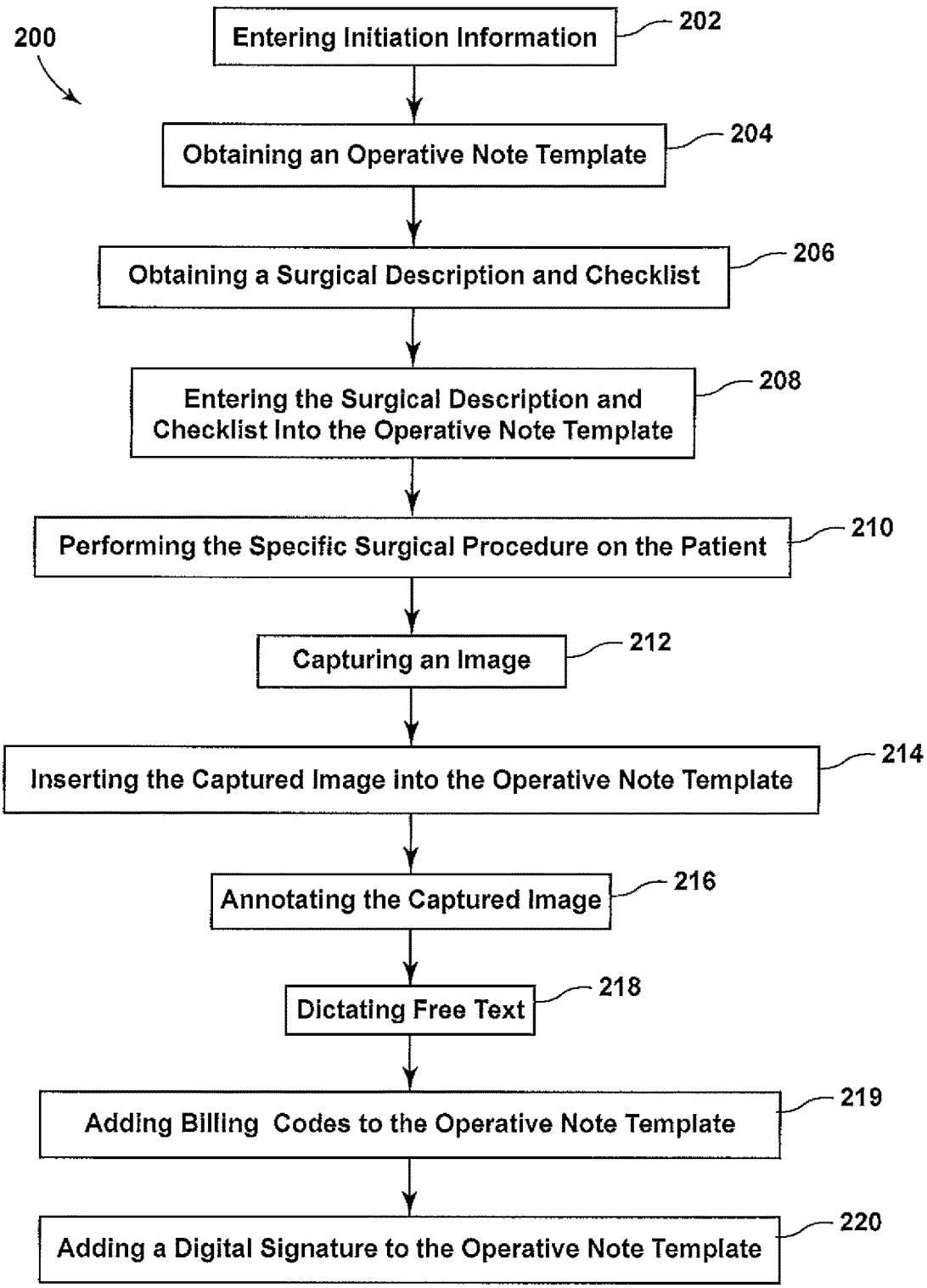
FIG. 6 illustrates a method of creating the surgical operative note during a specific surgical procedure on a patient using the schematic process of FIG. 5.

FIG. 6 illustrates a method 200 of creating the surgical operative note 100 during the specific surgical procedure on the patient 10 using the schematic process of FIG. 5. First, at step 202, the imaging system 12 is initiated by a surgeon 112 or other person in the surgical theater when the surgeon 112 or other person enters initiation information into the imaging system 12 by voice via the microphone 38, manually via the touchscreen monitor 23 or via other input devices 44. The initiation information includes entering the specific surgical procedure to be performed on the patient 10. The initiation information can also include the name of the surgeon 112. Once the initiation information is entered, the imaging system 12 obtains an operative note template from the documentation template database 84 at step 204, with the operative note template being used to form the surgical operative note 100. The operative note template can be customized for a particular hospital or location for the surgery, can be customized for the specific surgical procedure and/or can be customized for the particular surgeon 112 performing the specific surgical procedure.

Once the operative note template is selected in step 204, the surgical description and checklist 102 for the particular surgical procedure entered in step 202 is obtained from the surgical description and checklist database 86 at step 206 and entered into the operative note template at step 208. The surgical description and checklist 102 pertains to the particular surgical procedure being performed by the surgeon 112 and can include a checklist that the surgeon and/or other person can check before and during the surgery (e.g., by checking information to ensure that the correct patient is to be operated on, checking to ensure that the correct procedure is performed, checking to ensure that the surgery is being performed on the correct area of the patient 10, etc.). The surgical description and checklist 102 can also include a description and/or roadmap (i.e., the steps to be taken to perform the surgery) of the particular surgery being performed. The surgical description and checklist 102 can be customized for a particular hospital or location for the surgery and/or can be customized for the particular surgeon 112 performing the specific surgical procedure.

The method 200 of creating the surgical operative note 100 also includes performing the specific surgical procedure on the patient 10 at step 210. While the step 210 of performing the specific surgical procedure typically occurs after steps 202, 204, 206 and 208 are performed and the creation of the surgical operative note 100 is begun, it is contemplated that the step of performing the specific surgical procedure can begin at any time before or after steps 202, 204, 206 and 208. During the step 210 of performing the specific surgical procedure on the patient 10, the surgeon 112 can capture images 104 at step 212 from the video camera 14 to be inserted into the operative note template to form the surgical operative note 100. The images 104 can be captured in any manner in which a still image 104 is taken and inserted into the operative note template. For example, an icon on the touchscreen monitor 23 can be touched to capture the still image 104, a button can be pressed to capture the still image 104 (e.g., one of the buttons 36 on the video camera 14, a button on the headset 40, a button on a remote control, an icon on the touchscreen monitor 23, etc.), or the surgeon 112 (or other person in the surgical theater) can utter a particular phrase (e.g., "capture image" or "take picture") to capture the still image 104. After the image 104 is captured at step 212, the image 104 is inserted into the operative note template at step 214.

In the illustrated example, directly after insertion of the image 104 into the operative note template, the image 104 is annotated at step 216 to insert the annotation 106 into the operative note template. In the illustrated embodiment, the annotations 106 that can be inserted into the operative note template to be associated with the selected image 104 are taken from an index of annotations 106 stored in the annotation module 62 of the VCS 16 and/or the annotation module 82 of the ICS 20. The index of annotations 106 is limited and customized for a particular hospital or location for the surgery, for the specific specialty of the procedure, for the specific surgical procedure and/or for the particular surgeon 112 performing the specific surgical procedure. During the step 210 of performing the specific surgical procedure, the surgeon 112 issues a voice command (e.g., by stating "annotate image") to bring up the index of annotations 106 or uses a voice command to directly call up one of the annotations 106 from the index of annotations 106 (e.g., by stating "insert annotation number 5"). In the illustrated embodiment, surgeon 112 must use one of the annotations 106 from the index of annotations 106 to annotate the image 104 and is not able to freely dictate the annotation 106 of the image 104. It is contemplated that the annotation 106 can be text or a graphical object positioned adjacent the image 104 or can be superimposed over the image 104.

At any time during the method 200 of creating the surgical operative note 100, the surgeon 112 can dictate freely at step 218, with the dictation being converted into dictated text 110 and entered into the operative note template in the free text area 108. The surgeon 112 can begin step 218 by making an utterance or speaking a command that activates the VCS 16 (e.g., by stating "free speech"). The operative note template can also have the further text area 111 for the predetermined text 113. The predetermined text 113 can be any text associated with the patient 10, the surgeon 112 or the specific surgical procedure. For example, the predetermined text 113 can be patient information (obtained from a Hospital Information System through the network interface 72), a reference to the surgeon's website, or a url to the patient's record online automatically entered when the initiation information is entered at step 202.

In the illustrated example, the predetermined text 113 can also include billing codes obtained from the surgical billing code database 99 and added to the predetermined text 113 at step 219. During step 219, the billing code extraction engine 101 will add billing codes retrieved from the surgical billing code database 99 upon the addition of the annotation during step 216 or upon addition of certain text during step 218. The index of annotations 106 can tie a particular billing code to some or all of the annotations in the index of annotations 106. For example, if the annotation is "osteoarthritis," the billing code extraction engine 101 can automatically add the billing code for this disease (e.g., 715 using ICD 9) to the predetermined text 113 when the annotation "osteoarthritis" is added during step 216. Similarly, the billing code extraction engine 101 can continually search the dictated text 110 to see if a particular word is added to the free text area 108, and if so, automatically add a billing code to the predetermined text 113. For example, if the word "osteoarthritis" is added as dictated text 110 to the free text area 108, the billing code extraction engine 101 can automatically add the billing code for this disease (e.g., 715 using ICD 9) to the predetermined text 113.

The method 200 of creating the surgical operative note 100 can also include a step 220 of adding a digital signature 300 to the operative note template. The digital signature 300 is a signature of the surgeon 112 approving of the surgical operative note 100 created during the method 200 of creating the surgical operative note 100. The digital signature 300 can include the surgeon's name, and a password may be required by the surgeon 112 to properly authenticate the digital signature 300. Digital signatures 300 and their implementation are well known to those skilled in the art.

Non-text annotations, such as graphical objects, can also be associated with the image 104 in a similar manner. In that case, it is desirable to have a set of predefined annotation objects from which the user can select, such as a pointer or a hollow shape to point to or outline a feature of interest. The selected annotation object can be associated with the image in a similar manner as described above.

It is contemplated that the microphone and/or a camera of the imaging system 12 can be connected to wearable technology worn by the surgeon. The wearable technology can include a camera that captures an image taken from the surgeon's point of view or perspective. Furthermore, the wearable technology can include the VCS 16, with the wearable technology communicating wirelessly with a separate ICS 20. The wearable technology can convert the speech of the surgeon into text that can be commands for controlling the ICS 20 and/or for controlling the ICS 20 to create the surgical operative note 100 using the method 200 described above. The wearable technology can also include a touch pad (e.g., programmable) that allows the surgeon to touch the wearable technology to capture the image for insertion into the surgical operative note 100. An example of the wearable technology is Google Glass sold by Google Inc. of Mountain View, Calif.

By using the method 200 of creating the surgical operative note 100 during the specific surgical procedure on the patient 10 discussed above, a complete surgical operative note 100 can be completed efficiently and simultaneously with completion of the surgery on the patient 10. Furthermore, information developed and compiled before surgery can be added to the operative note in an efficient manner to thereby reduce the time and effort of the surgeon in making the operative note 100. Accordingly, the time and effort expended to create and authenticate the surgical operative note 100 can be greatly reduced using the method of the present invention.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of creating a surgical operative note during a specific surgical procedure on a patient, the method comprising:
   creating a plurality of surgical checklists before initiation of the specific surgical procedure, each surgical checklist being associated with a different surgical procedure;
   creating an index of image specific annotations that correspond to the specific surgical procedure before initiation of the specific surgical procedure and wherein the image specific annotations include at least one text annotation;
   obtaining an electronic surgical operative note template;
   inserting a surgical checklist of the plurality of surgical checklists that is associated with the specific surgical procedure on the patient into the electronic surgical operative note template;
   capturing, during the specific surgical procedure, an image of the patient;
   inserting, during the specific surgical procedure, the image of the patient into the electronic surgical operative note template;
   displaying, during the specific surgical procedure, the image of the patient and at least a portion of the index of image specific annotations;
   receiving a voice command during the specific surgical procedure indicating a selection of at least one of the image specific annotations from the index of image specific annotations to associate with the image of the patient in the electronic surgical operative note template; and
   in response to receiving the voice command, inserting the selected at least one of the image specific annotations into the electronic surgical operative note template and displaying, during the specific surgical procedure, the selected at least one of the image specific annotations together with the image of the patient.

2. The method of creating the surgical operative note of claim 1, further including:
   receiving dictated information related to the specific surgical procedure during the specific surgical procedure; and
   inserting text generated from the dictated information into the electronic surgical operative note template at a location in the electronic surgical operative note template spaced from the at least one of the image specific annotations;
   wherein inserting the text into the electronic surgical operative note template occurs during the specific surgical procedure.

3. The method of creating the surgical operative note of claim 2, further including:
   adding at least one billing code to the electronic surgical operative note template corresponding to the specific surgical procedure, wherein the at least one billing code is automatically added to the electronic surgical operative note template during the step of inserting the text into the electronic surgical operative note template.

4. The method of creating the surgical operative note of claim 1, further including:
adding a digital signature to the electronic surgical operative note template.

5. The method of creating the surgical operative note of claim 1, further including:
adding at least one billing code to the electronic surgical operative note template corresponding to the specific surgical procedure.

6. The method of creating the surgical operative note of claim 5, wherein:
the at least one billing code is automatically added to the electronic surgical operative note template during insertion of the at least one of the image specific annotations into the electronic surgical operative note template.

7. The method of claim 1, wherein index of image specific annotations is limited for a particular hospital for the specific surgical procedure, for a particular location for the specific surgical procedure, for a specialty of the specific surgical procedure, or for a particular surgeon performing the specific surgical procedure.

8. The method of claim 1, further comprising, prior to displaying the at least a portion of the index of image specific annotations, receiving a voice command to display the at least a portion of the index of image specific annotations, and displaying the at least a portion of the index of image specific annotations in response.

9. A method of creating a surgical operative note during a specific surgical procedure on a patient, the method comprising:
creating surgical information before initiation of the specific surgical procedure;
creating an index of image specific annotations that correspond to the specific surgical procedure before initiation of the specific surgical procedure and wherein the image specific annotations include at least one text annotation;
obtaining an electronic surgical operative note template;
inserting the surgical information into the electronic surgical operative note template;
capturing, during the specific surgical procedure, an image of the patient;
inserting, during the specific surgical procedure, the image of the patient into the electronic surgical operative note template;
displaying, during the specific surgical procedure, the image of the patient and at least a portion of the index of image specific annotations;
receiving a voice command during the specific surgical procedure indicating a selection of at least one of the image specific annotations from the index of image specific annotations to associate with the image of the patient in the electronic surgical operative note template; and
in response to receiving the voice command, inserting the selected at least one of the image specific annotations into the electronic surgical operative note template and displaying, during the specific surgical procedure, the selected at least one of the image specific annotations together with the image of the patient;
receiving, during the specific surgical procedure, dictated information related to the specific surgical procedure; and
inserting text generated from the dictated information into the electronic surgical operative note template at a location in the electronic surgical operative note template spaced from the at least one of the image specific annotations;
wherein inserting the text into the electronic surgical operative note template occurs during the specific surgical procedure.

10. The method of creating the surgical operative note of claim 9, further including:
adding a digital signature to the electronic surgical operative note template.

11. The method of creating the surgical operative note of claim 9, wherein:
the surgical information includes at least one of a checklist of steps to take for the specific surgical procedure and a description of the specific surgical procedure.

12. The method of creating the surgical operative note of claim 9, further including:
adding at least one billing code to the electronic surgical operative note template corresponding to the specific surgical procedure.

13. The method of creating the surgical operative note of claim 12, wherein:
the at least one billing code is automatically added to the electronic surgical operative note template during insertion of the at least one of the image specific annotations into the electronic surgical operative note template.

14. The method of creating the surgical operative note of claim 12, wherein:
the at least one billing code is automatically added to the electronic surgical operative note template during the step of inserting the text into the electronic template.

15. The method of claim 9, wherein index of image specific annotations is limited for a particular hospital for the specific surgical procedure, for a particular location for the specific surgical procedure, for a specialty of the specific surgical procedure, or for a particular surgeon performing the specific surgical procedure.

16. The method of claim 9, further comprising, prior to displaying the at least a portion of the index of image specific annotations, receiving a voice command to display the at least a portion of the index of image specific annotations, and displaying the at least a portion of the index of image specific annotations in response.

* * * * *